(12) United States Patent
Ales et al.

(10) Patent No.: US 8,274,393 B2
(45) Date of Patent: Sep. 25, 2012

(54) REMOTE DETECTION SYSTEMS FOR ABSORBENT ARTICLES

(75) Inventors: Thomas Michael Ales, Neenah, WI (US); Andrew Mark Long, Appleton, WI (US); Chuck R. Tomsovic, Winneconne, WI (US); Davis-Dang H. Nhan, Appleton, WI (US); Shirlee Ann Weber, Neenah, WI (US); Jason C. Cohen, Appleton, WI (US); Shawn Jeffrey Sullivan, Neenah, WI (US); Xuedong Song, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 518 days.

(21) Appl. No.: 12/347,539

(22) Filed: Dec. 31, 2008

(65) Prior Publication Data

US 2010/0164733 A1 Jul. 1, 2010

(51) Int. Cl.
*G08B 21/00* (2006.01)
(52) U.S. Cl. ........................................ 340/604; 604/361
(58) Field of Classification Search .................. 340/604, 340/603, 605, 573.5; 604/361, 378
See application file for complete search history.

(56) References Cited

U.S. PATENT DOCUMENTS

| | | | |
|---|---|---|---|
| 4,068,221 A * | 1/1978 | McClintock | 340/604 |
| 4,100,324 A | 7/1978 | Anderson et al. | |
| 4,191,950 A * | 3/1980 | Levin et al. | 340/604 |
| 4,571,750 A | 2/1986 | Barry | |
| 4,704,116 A | 11/1987 | Enloe | |
| 4,768,023 A | 8/1988 | Xie | |
| 4,926,871 A | 5/1990 | Ganguly et al. | |
| 4,940,464 A | 7/1990 | Van Gompel et al. | |
| 5,284,703 A | 2/1994 | Everhart et al. | |
| 5,322,067 A | 6/1994 | Prater et al. | |
| 5,350,624 A | 9/1994 | Georger et al. | |
| 5,454,376 A | 10/1995 | Stephens et al. | |
| 5,486,166 A | 1/1996 | Bishop et al. | |
| 5,490,846 A | 2/1996 | Ellis et al. | |
| 5,766,389 A | 6/1998 | Brandon et al. | |
| 5,820,973 A | 10/1998 | Dodge, II et al. | |

(Continued)

FOREIGN PATENT DOCUMENTS

WO WO 00/37009 A2 6/2000

OTHER PUBLICATIONS

International Search Report and Written Opinion, PCT/IB2009/055120, dated Aug. 23, 2010.

*Primary Examiner* — John A Tweel, Jr.
(74) *Attorney, Agent, or Firm* — Dority & Manning, P.A.

(57) ABSTRACT

Signaling systems are disclosed that indicate a change in an absorbent article, such as the presence of a body fluid. The various different signaling systems disclosed do not include any conductive elements contained on the interior of the article as were required in the past. Instead, the changes are monitored from the outer cover of the article. In one embodiment, for instance, conductive zones are formed directly into the outer cover for forming the signaling system. Alternatively, a sensor may be mounted to the outer cover of the article for monitoring changes within the article. The sensor may comprise, for instance, a temperature sensor, a conductivity sensor, an optical sensor, a vibration sensor, a humidity sensor, a material expansion sensor, a chemical sensor, or the like.

37 Claims, 11 Drawing Sheets

U.S. PATENT DOCUMENTS

| | | | |
|---|---|---|---|
| 5,845,644 A * | 12/1998 | Hughes et al. | 128/885 |
| 6,110,111 A | 8/2000 | Barnard | |
| 6,163,262 A | 12/2000 | Wu | |
| 6,200,250 B1 * | 3/2001 | Janszen | 604/361 |
| 6,359,190 B1 | 3/2002 | Ter-Ovanesyan et al. | |
| 6,484,053 B2 | 11/2002 | Leelamanit et al. | |
| 6,580,013 B1 | 6/2003 | Belloso | |
| 6,645,190 B1 | 11/2003 | Olson et al. | |
| 6,677,859 B1 | 1/2004 | Bensen | |
| 6,731,215 B2 * | 5/2004 | Harms et al. | 340/605 |
| 6,929,819 B2 | 8/2005 | Underhill et al. | |
| 7,394,391 B2 * | 7/2008 | Long | 340/573.5 |
| 7,477,156 B2 | 1/2009 | Long et al. | |
| 7,833,177 B2 | 11/2010 | Long et al. | |
| 2003/0028165 A1 * | 2/2003 | Curro et al. | 604/378 |
| 2005/0156744 A1 * | 7/2005 | Pires | 340/573.5 |
| 2005/0251036 A1 | 11/2005 | Abuhamad | |
| 2007/0024457 A1 * | 2/2007 | Long et al. | 340/605 |
| 2007/0048709 A1 | 3/2007 | Ales, III et al. | |
| 2007/0142799 A1 * | 6/2007 | Ales et al. | 604/361 |
| 2008/0048786 A1 | 2/2008 | Feldkamp et al. | |
| 2008/0054408 A1 * | 3/2008 | Tippey et al. | 257/621 |
| 2008/0077040 A1 | 3/2008 | Ales et al. | |
| 2008/0077042 A1 | 3/2008 | Feldkamp et al. | |
| 2008/0132859 A1 * | 6/2008 | Pires | 604/361 |
| 2008/0243099 A1 | 10/2008 | Tippey et al. | |
| 2008/0266122 A1 | 10/2008 | Ales et al. | |
| 2009/0005748 A1 * | 1/2009 | Ales et al. | 604/361 |
| 2009/0062756 A1 | 3/2009 | Long et al. | |
| 2009/0157025 A1 | 6/2009 | Song et al. | |
| 2009/0326417 A1 * | 12/2009 | Ales et al. | 604/361 |
| 2010/0114047 A1 | 5/2010 | Song et al. | |

* cited by examiner

REMOTE DETECTION SYSTEMS FOR ABSORBENT ARTICLES

BACKGROUND

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent articles, especially those sold under the tradename HUGGIES™ by the Kimberly-Clark Corporation, are so efficient at absorbing liquids that it is sometimes difficult to tell whether or not the absorbent article has been insulted with a body fluid.

Accordingly, various types of electronic moisture or wetness indicators have been suggested for use in absorbent articles. The wetness indicators may include alarm devices that are designed to assist parents or attendants identify a wet diaper condition early on. The devices can produce an audible, tactile, electromagnetic or visual signal.

In some embodiments, for instance, conductive threads or foils have been placed in the absorbent articles that extend from the front of the article to the back of the article. The conductive materials serve as conductive leads for a signaling device and form an open circuit in the article that can be closed when a body fluid, such as urine, closes the circuit.

Incorporating conductive leads into absorbent articles, however, has caused various problems. For example, absorbent articles are typically mass produced on very fast moving machinery. Incorporating conductive leads into an absorbent article at conventional machine speeds has been problematic.

In addition, packaged absorbent articles are typically fed through a metal detector to ensure that there are no foreign objects contained in the package. If the conductive leads are made from or contain a metal, the metal detector may be activated registering a false positive. The incorporation of metallic materials into absorbent articles can also cause problems for those wearing the garments when attempting to pass through security gates that include metal detectors.

In view of the above, a need currently exists for a signaling system for an absorbent article that does not require conductive elements containing metal or other devices to be inserted into the interior of the article.

SUMMARY

The present disclosure is generally directed to various signaling systems that are particularly well suited for use in conjunction with absorbent articles. The signaling systems, for instance, may be connected to a signaling device that can be configured to emit a signal, such as an audible, tactile, electromagnetic or visual signal, for indicating to a user that a body fluid is present in the absorbent article. For example, in one embodiment, the absorbent article comprises a diaper and the signaling system is configured to indicate the presence of urine or a bowel movement. In other absorbent articles, however, the signaling systems may be configured to indicate the presence of yeast or metabolites.

More particularly, the present disclosure is directed to signaling systems for absorbent articles that can detect the presence of a body fluid without having to place or insert conductive elements into the interior of the article. For instance, in one embodiment, a sensor may be mounted to an exterior surface of the absorbent article that is capable of sensing a change on the interior of the article that indicates the presence of a body fluid, such as urine. In an alternative embodiment, conductive zones can be formed on the outer cover of the absorbent article that can then be connected to a signaling device. Once a body fluid, such as urine, contacts the outer cover, an electrical connection is formed between the conductive zones on the outer cover which then activates the signaling device.

For example, in one embodiment, the present disclosure is directed to an absorbent article comprising an outer cover having an interior surface and an exterior surface. An absorbent structure is positioned adjacent to the interior surface. In one embodiment, the absorbent article can further include a liquid permeable liner. The absorbent structure may be positioned in between the outer cover and the liner.

In accordance with the present disclosure, the outer cover can include a first conductive zone spaced from and discrete from a second conductive zone. Each conductive zone may comprise an area on the outer cover that defines a plurality of apertures. The apertures, for instance, may extend through the outer cover. The apertures are covered by a conductive composition. The conductive composition not only makes the different zones conductive but also can be used to seal the apertures for preventing liquids contacting the interior surface of the outer cover from leaking through to the exterior surface. Use of the apertures, however, allows liquids contacting the interior surface of the outer cover to make an electrical connection between the two conductive zones. When an electrical connection is made between the two conductive zones, a circuit is formed that can then activate a signaling device. The signaling device, for instance, may emit an audible or visual signal that indicates the presence of a body fluid.

The adhesive composition that is used to cover the apertures can vary depending upon the particular application. For instance, in one embodiment, a conductive dye or a conductive adhesive may be used. The size of the apertures can also vary. The apertures, in one embodiment, can have a diameter of generally from about 0.1 mm to about 1.5 mm, such as from about 0.5 mm to about 1 mm. Each conductive zone can contain from about 10 apertures per $cm^2$ to about 50 apertures per $cm^2$.

The absorbent article can include a front region, a back region, and a crotch region positioned in between the front region and the back region. The first conductive zone and the second conductive zone can extend from the front or back region into the crotch region.

The signaling device can comprise any suitable device capable of making an electrical connection to the first and second conductive zones and that is able to produce a signal when desired. In one embodiment, the signaling device may comprise a device that is intended to be reusable such that the device is removed from the absorbent article after the article is worn. For instance, in one embodiment, the signaling device may comprise a clip that goes over an edge of the absorbent article and makes an electrical connection with the two conductive zones. Alternatively, the signaling device may include conductive hook-type members that can attach to the outer cover of the absorbent article and also make an electrical connection with the first and second conductive zones. In still another embodiment, the signaling device may include a conductive adhesive that attaches the device to the absorbent article.

The signaling device can also be configured to be disposed with the product. In this embodiment, for instance, the signaling device can be directly incorporated into the outer cover of the absorbent article.

In an alternative embodiment of the present disclosure, the absorbent article includes a signaling system that comprises a sensor. The sensor is configured to be attached to the outer cover of the absorbent article and is configured to sense a change in a condition within the absorbent structure. In this embodiment, the sensor may comprise, for instance, a temperature sensor, a conductivity sensor, a humidity sensor, a vibration sensor, a chemical sensor, or a material expansion sensor. The sensor can be placed in communication with a signaling device. Once a change within the interior of the absorbent article is detected, the signaling device can be configured to emit a signal that indicates a body fluid is present in the absorbent article.

When the sensor comprises a temperature sensor, for instance, the temperature sensor can be attached or placed in close proximity to the exterior surface of the outer cover of the absorbent article for monitoring the temperature within the article. In one embodiment, the signaling device can be configured to emit a signal when the temperature sensor senses a temperature within the garment of greater than about 32° C., such as greater than about 34° C. In an alternative embodiment, the signaling device may be configured to emit a signal based on a rapid increase in temperature. For instance, the signaling device may be configured to emit a signal when the temperature inside the absorbent article increases more than about 8° C. in less than about one minute, such as less than about 30 seconds.

In still another embodiment, the signaling system may include more than one temperature sensor for sensing the temperature inside the absorbent article and for measuring the temperature outside the absorbent article. In this embodiment, the signaling device may be configured to emit a signal when the difference between the temperature inside the article and the temperature outside the article exceeds a certain preset limit. The preset limit, for instance, may be a temperature differential of greater than about 8° C., such as greater than about 10° C., such as greater than about 12° C.

Instead of using a temperature sensor, in one embodiment, the signaling system may include a conductivity sensor that senses changes in conductivity within the article. Urine, for instance, is a conductive fluid. Thus, insulting the absorbent article with urine will create a change in conductivity. In one embodiment, for instance, the conductivity sensor may comprise an RF induction coil that senses changes in impedance. The change in impedance may be measured by an oscillator.

In still another embodiment, the sensor may comprise a humidity sensor. Insulting an absorbent article with urine will cause the humidity within the article to increase. These humidity changes can be monitored outside the absorbent article, especially when the outer cover is breathable. In one embodiment, for instance, the signaling device may be configured to emit a signal when the humidity within the garment increases by more than about 10% in less than about 30 seconds. Alternatively, the signaling system may include a first humidity sensor that senses humidity within the absorbent article and a second humidity sensor that senses humidity on the outside of the article. In this embodiment, the signaling device may be configured to emit a signal when the difference in humidity between the inside of the article and the outside of the article reaches a preset limit or the rate of change of humidity between the two varies.

In still another embodiment, the sensor contained in the signaling system may comprise a vibration sensor that senses vibrations within the absorbent article, such as sound. For instance, in one embodiment, the vibration sensor may comprise a microphone. In this embodiment, the absorbent article may contain a noise producing composition that produces noise when wetted. The vibration sensor can be configured to sense the vibrations emitted by the noise producing composition thus causing the signaling device to emit a signal.

In still another embodiment, the sensor may comprise a chemical sensor that senses a particular chemical within the absorbent article for indicating that a body fluid is present, such as urine. For example, in this embodiment, the absorbent article may contain a chemical indicating composition that emits a chemical species when wetted. The chemical sensor can be configured to sense the existence of the chemical species. Thus, when the absorbent article is wetted, the chemical indicating composition produces the chemical species which is sensed by the chemical sensor causing the signaling device to emit a signal. The chemical species, for instance, may comprise a gas or a liquid. In one embodiment, the chemical species may comprise a volatile organic compound and the chemical sensor may be configured to detect the presence of volatile inorganic compounds. These compounds can be sensed from the exterior surface of the outer cover of the absorbent article, especially when the outer cover is breathable.

In other embodiments, the chemical species that may be produced by the chemical indicating composition may comprise carbon dioxide or nitrogen. A chemical sensor can then be used that is capable of sensing the presence of carbon dioxide or nitrogen.

Alternatively organic volatile gases which are constituents of urine can be directly measured, such as ammonia. In this embodiment, a chemical indicating composition may not be necessary.

In yet another embodiment of the present disclosure, the sensor contained in the signaling system may comprise a material expansion sensor. In this embodiment, the sensor is configured to indicate when a particular location of the absorbent article has expanded. Such expansions occur, for instance, when the article has been wetted and the article must then support the weight of the body fluid. In these embodiments, particular elements of the absorbent article in the crotch region may expand in size. The material expansion sensor may be configured to monitor and sense these expansions. For instance, in one embodiment, the material expansion sensor may comprise a strain gauge that activates the signaling device when the material expansion is sensed.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
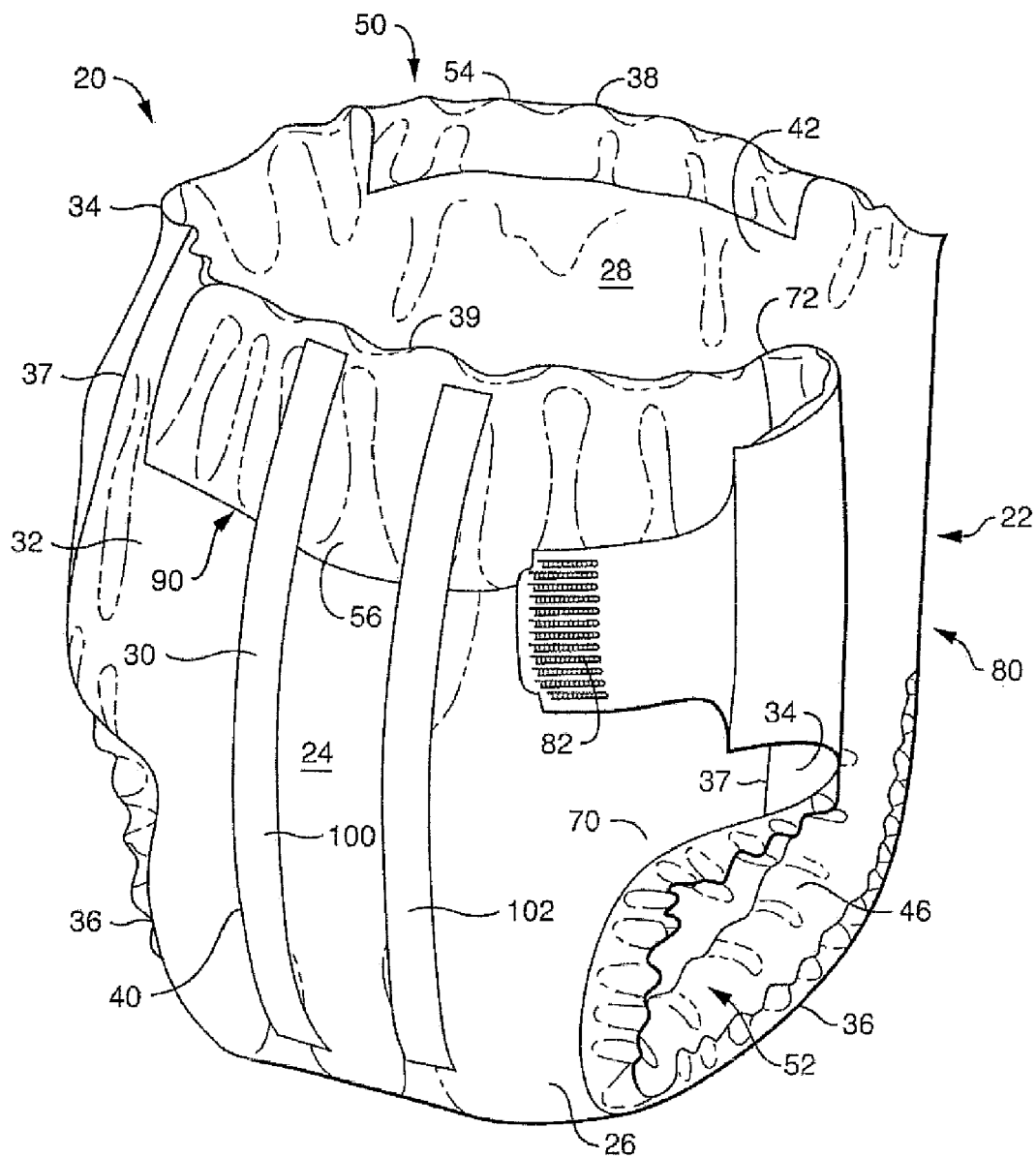
FIG. 1 is a rear perspective view of one embodiment of an absorbent article made in accordance with the present invention.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to signaling systems for absorbent articles that indicate to a user when a body fluid has insulted the article. For example, in one embodiment, the signaling system is designed to emit a signal when urine is detected in the absorbent article. The absorbent article may be, for instance, a diaper, a training pants, an incontinence product, a feminine hygiene product, a medical garment, a bandage, and the like.

Of particular advantage, signaling systems made in accordance with the present disclosure can sense the presence of a body fluid within the absorbent article without having to construct the absorbent article with any elements or sensors contained in the interior of the article. In the past, for instance, metallic conductive leads were typically placed within the interior of the absorbent article. The signaling systems of the present disclosure, on the other hand, can sense the presence of a body fluid from an exterior surface of the article which can greatly simplify the incorporation of the signaling system into the article.

In accordance with the present disclosure, the signaling system can have various configurations and designs. In one embodiment, for instance, conductive zones can be integrated into an outer cover of an absorbent article. The conductive zones can be constructed on the outer cover so that they will be in contact with any conductive fluid that may be contained inside the absorbent article, such as a body fluid.

For example, in one embodiment, the outer cover may include apertured zones that are then sealed with a conductive composition to create the conductive zones. The outer cover can include at least two separate and discrete conductive zones or may contain more conductive zones as desired. The conductive zones can be placed in communication with a signaling device. In this configuration, a conductive fluid, such as urine, contained with the absorbent article will form a conductive bridge between the two conductive zones and thereby closing a circuit that then activates the signaling device.

Figure 2:
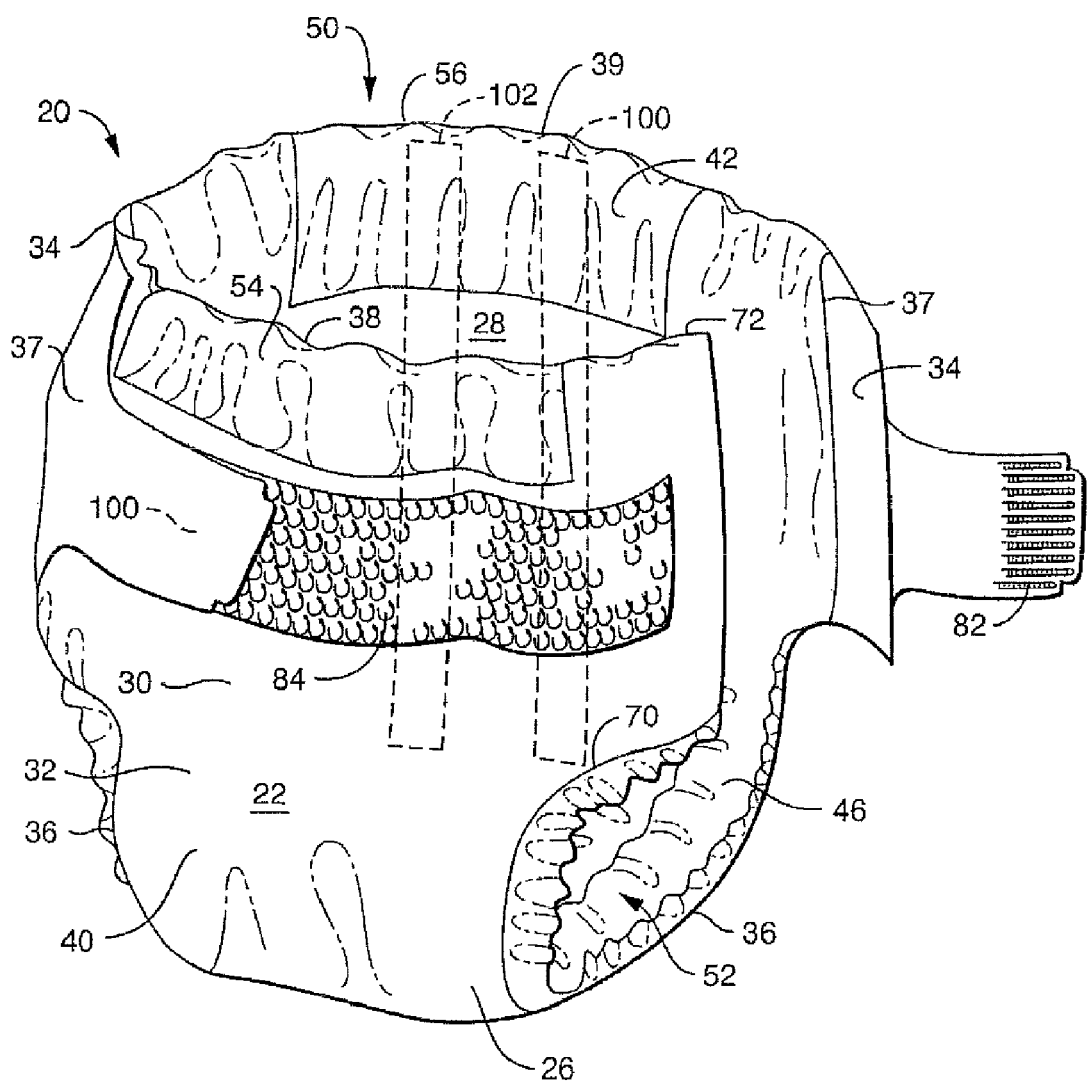
FIG. 2 is a front perspective view of the absorbent article illustrated in FIG. 1.

Referring to FIGS. 1 and 2, for exemplary purposes, an absorbent article 20 that may be used in conjunction with signaling systems of the present disclosure is shown. The absorbent article 20 may or may not be disposable. It is understood that the present invention is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing absorbent articles such as the diaper 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
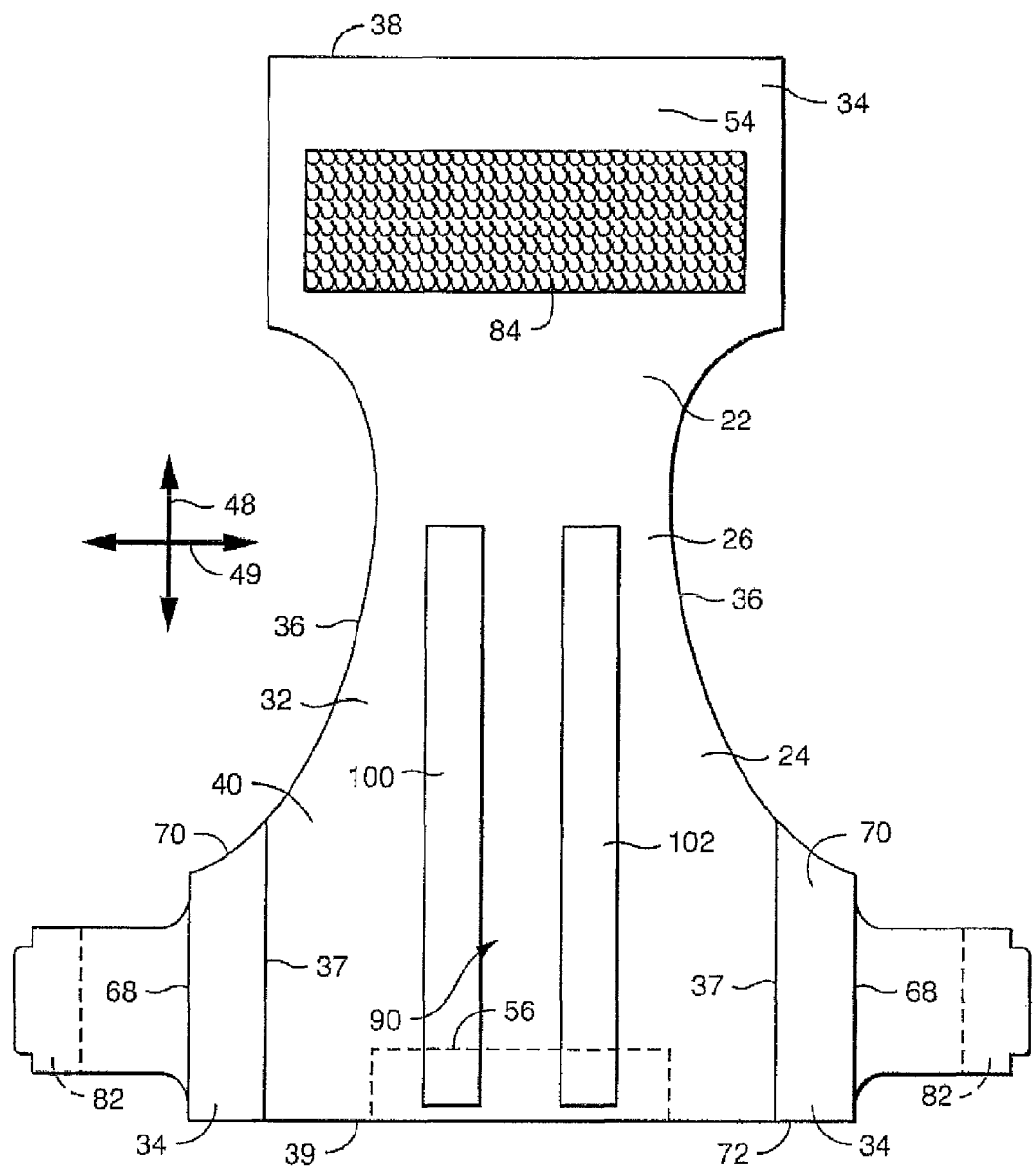
FIG. 3 is a plan view of the absorbent article shown in FIG. 1 with the article in an unfastened, unfolded and laid flat condition showing the surface of the article that faces away from the wearer.
Figure 4:
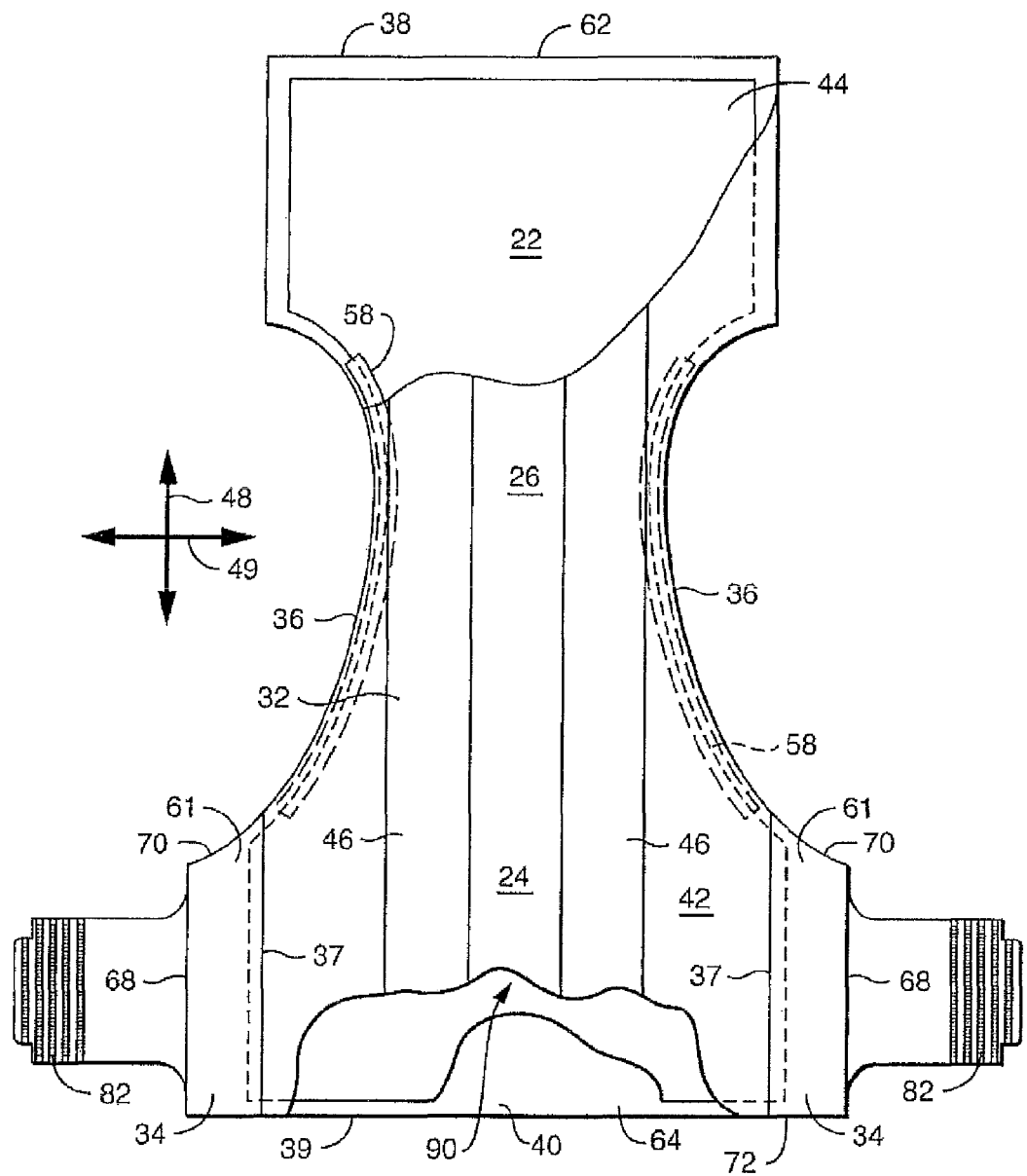
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is particularly directed to incorporating a signaling system, such as a wetness or urine sensing system into the absorbent article 20. In this regard, as shown in FIGS. 1-4, the absorbent article 20 includes a first conductive zone 100 spaced from a second conductive zone 102. In accordance with the present disclosure, the first conductive zone 100 and the second conductive zone 102 are integral with or otherwise formed on the outer cover 40 of the absorbent article 20.

Figure 6:
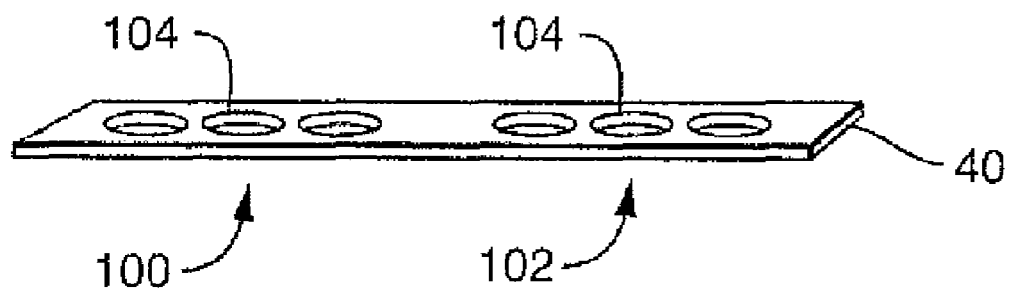
FIG. 6 is an exemplary drawing of perforations that may be placed in an outer cover material for an absorbent article in accordance with the present disclosure.
Figure 7:
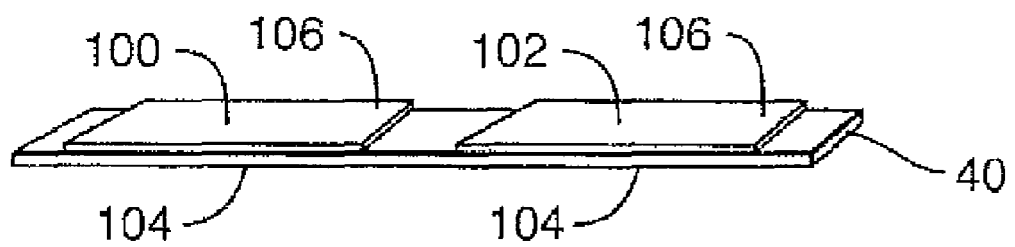
FIG. 7 is an exemplary drawing showing the perforated outer cover in FIG. 6 in which the perforations have been covered by a conductive composition in accordance with the present disclosure.

For example, referring to FIGS. 6 and 7, one manner for incorporating conductive zones into the outer cover 40 is shown. As illustrated in FIG. 6, the conductive zones 100 and 102 may comprise areas on the outer cover 40 where the outer cover has been perforated. For example, as shown, each of the zones includes apertures 104 that extend through the outer cover 40. The apertures can be formed into the outer cover using any suitable technique. For example, in one embodiment, the apertures can be formed in the outer cover using needles or any other suitable perforating equipment.

The size and density of the apertures contained in the conductive zones can vary depending upon the particular application. In one embodiment, for instance, the apertures can have a size of from about 0.1 mm to about 1.5 mm, such as from about 0.25 mm to about 1 mm. In addition, the apertures can be present in an amount from about 10 apertures per $cm^2$ to about 50 apertures per $cm^2$. The above dimensions, however, are merely exemplary and can vary depending upon the particular application.

As shown in FIG. 7, the apertures 104 are covered or sealed by a conductive composition 106. The conductive composition 106 provides the zones with their conductive characteristics or, in other words, the ability of the zones to carry electrical current. In general, any suitable conductive composition may be placed over the apertures. In one embodiment, for instance, a composition may be selected that provides the conductive zones with water impermeable properties so that urine or other body fluids do not leak out of the absorbent article. Examples of conductive compositions that may be used to cover the apertures include conductive inks, conductive adhesives, and the like. For example, various different conductive inks are available that contain silver. Conductive adhesives include any suitable conductive epoxy that is capable of attaching to the outer cover of the article.

In an alternative embodiment, the adhesive composition may be part of an adhesive or cohesive strip that is placed over the apertures. In one particular embodiment, the adhesive strip may be at least partially covered with a release liner. During use of the article, the release liner can be removed and a signaling device may be placed over the adhesive strip. Thus, the adhesive strip would not only adhere to the signaling device but would provide an electrical connection to the signaling device.

In the embodiment illustrated in FIGS. 1-4, the conductive zones extend from the back region 24 of the absorbent article to the crotch region 26 without intersecting. The first conductive zone 100 does not intersect the second conductive zone 102 in order to form an open circuit that may be closed, for instance, when a conductive fluid is positioned in between the conductive zones.

The conductive zones 100 and 102 may be incorporated into the outer cover 40 at any suitable location as long as the conductive zones are positioned so as to contact a body fluid that is absorbed by the absorbent article 20.

Figure 5:
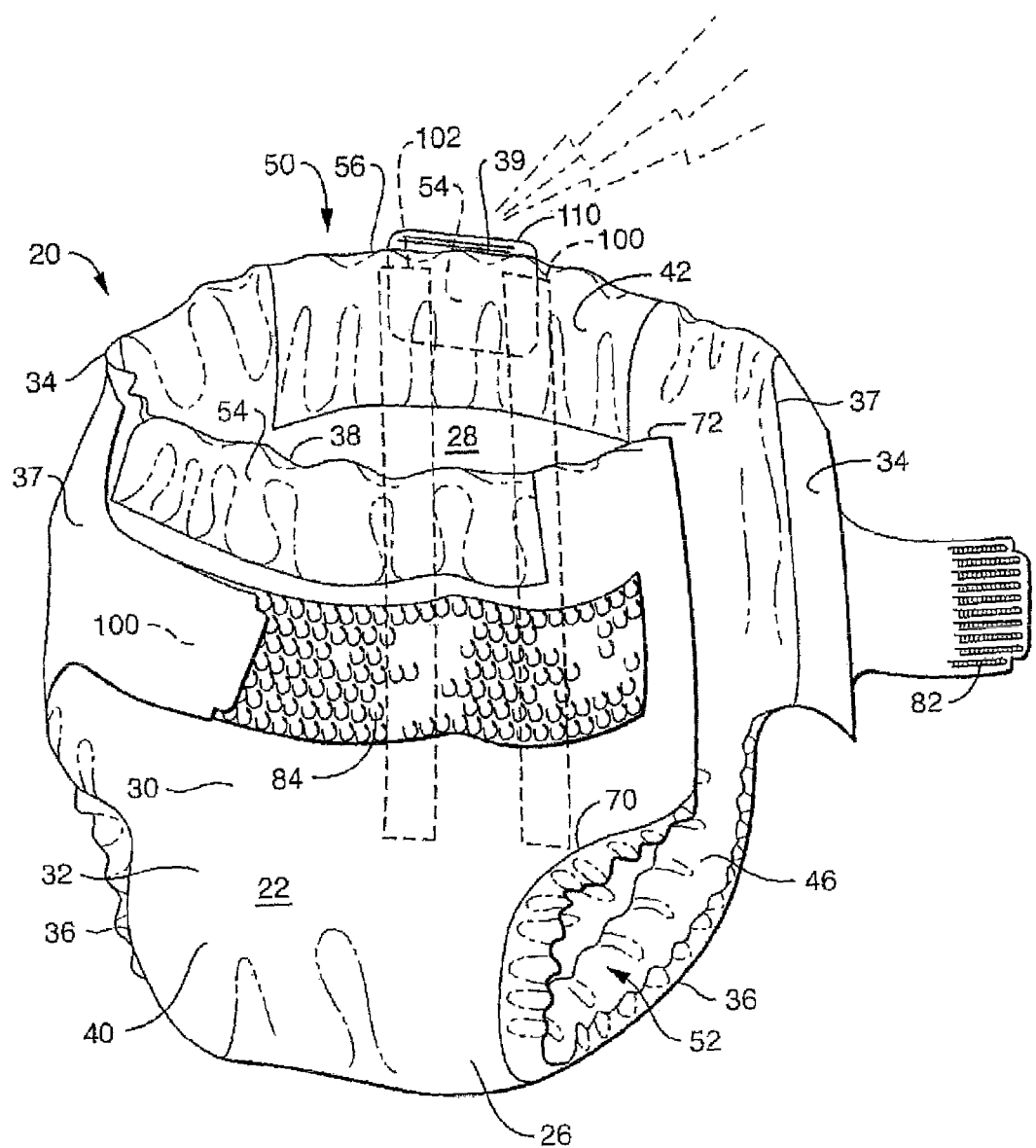
FIG. 5 is a perspective view of the embodiment shown in FIG. 1 further including one embodiment of a signaling device.

Referring to FIG. 5, for exemplary purposes, a signaling device 110 is shown attached to the conductive zones 100 and 102. The signaling device 110 includes a pair of opposing terminals that are electrically connected to the corresponding conductive zones. When a body fluid is present in the absorbent article 20, the open circuit formed by the conductive zones 100 and 102 is closed which, in turn, activates the signaling device 110. More particularly, when the absorbent article is wetted, the liquid generally wicks away from the crotch area and moves outwardly contacting the outer cover. In contacting the outer cover, the liquid contacts the conductive zones and forms a conductive bridge between the zones. The presence of the apertures increases the speed accuracy of the detection.

The signaling device 110 can emit any suitable signal in order to indicate to the user that the circuit has been closed. The signal, for instance, may comprise an audible signal, a tactile signal, an electromagnetic signal, or a visual signal. The audible signal, for instance, may be as simple as a beep or can comprise a musical tune. In still another embodiment, the signaling device may emit a wireless signal that then activates a remote device, such as a telephone or a pager.

Figure 8:
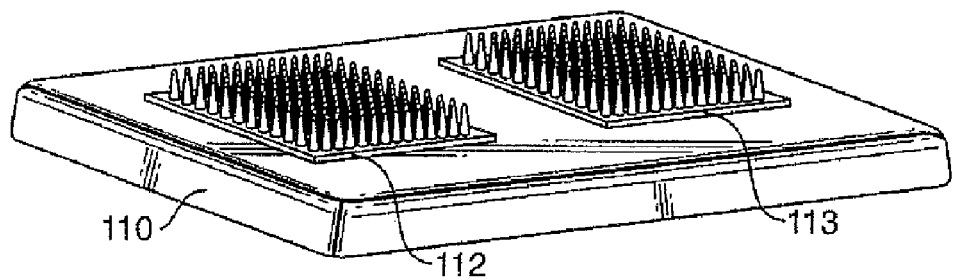
FIG. 8 is a perspective view of one embodiment of a signaling device that may be used in accordance with the present disclosure.
Figure 9:
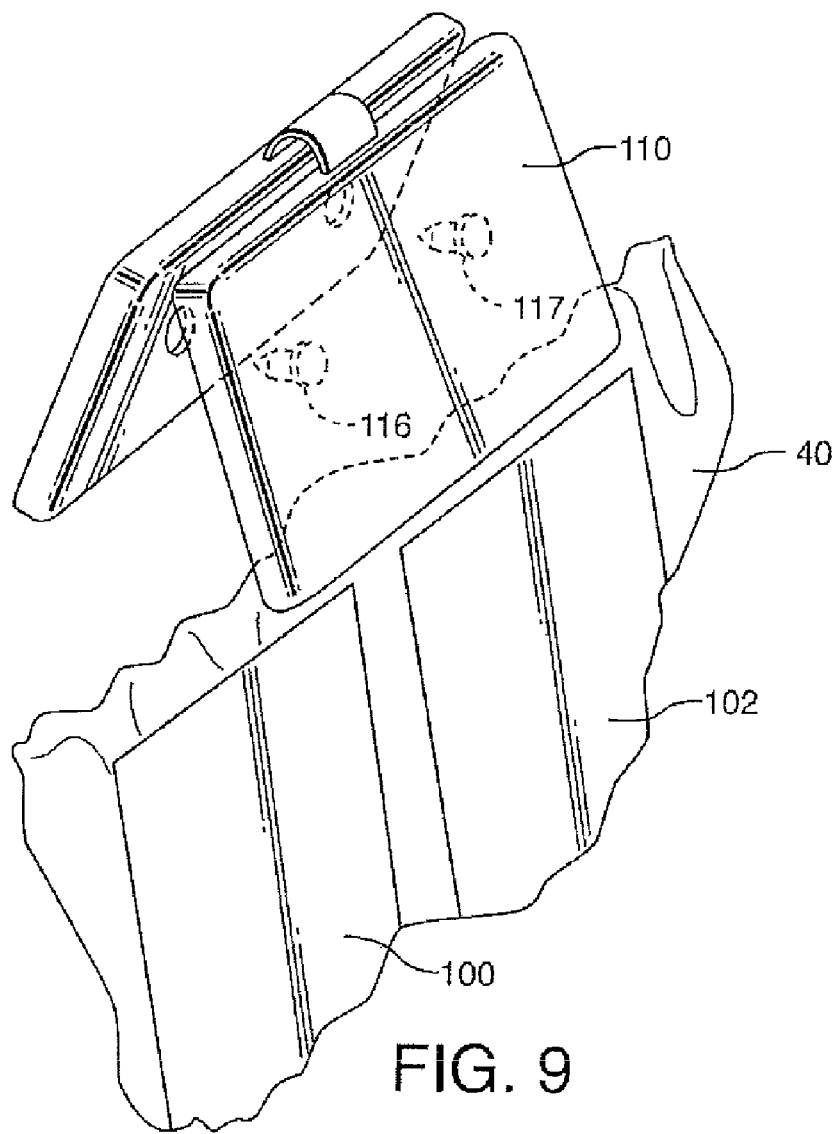
FIG. 9 is a perspective view of another embodiment of a signaling device that may be used in accordance with the present disclosure.
Figure 10:
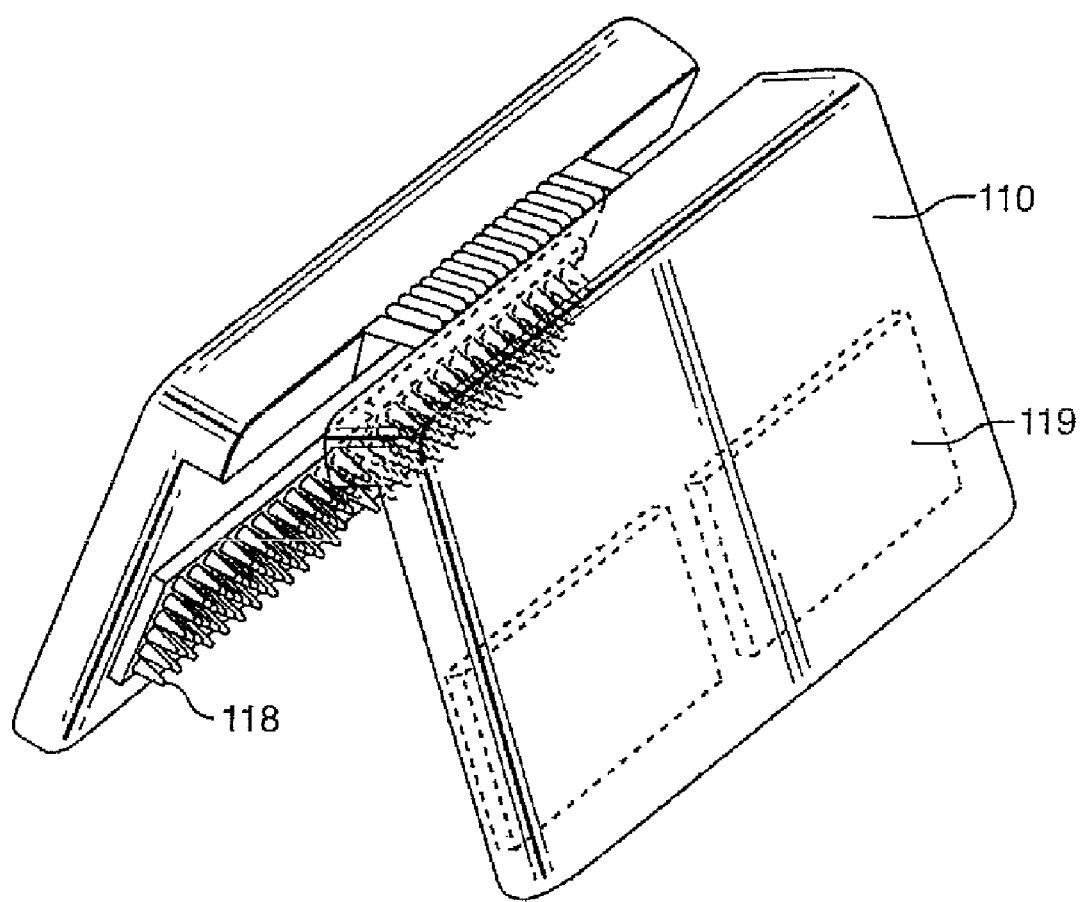
FIG. 10 is a perspective view of still another embodiment of a signaling device in accordance with the present disclosure.

Referring to FIGS. 8-10, various different embodiments of signaling devices that may be used in conjunction with the conductive zones shown in FIG. 5 are illustrated. Like reference numerals have been used to indicate similar elements. Referring to FIG. 8, a signaling device 110 is shown that is configured to make electrical connections to the conductive zones 100 and 102 as shown in FIG. 5. In this embodiment, the signaling device 110 includes a first hook-type conductive pad 112 spaced from a second hook-type conductive pad 113. The hook-type materials on the signaling device 110 are configured to not only attach the signaling device to the outer cover 40 but are also designed to make an electrical connection with the conductive zones 100 and 102. For instance, the outer cover 40 may be constructed from one or more nonwoven webs that can serve as loop-type material for the conductive hooks. Alternatively, a conductive loop-type material may be attached to the conductive zones for connecting to the signaling device.

Referring to FIG. 9, an alternative embodiment of a signaling device 110 is shown. In this embodiment, the signaling device 110 comprises a clip that goes over the edge of the absorbent article. The signaling device includes a first conductive pin 116 spaced from a second conductive pin 117. The pins 116 and 117 are for making electrical connections with the conductive zones 100 and 102 as shown.

Referring to FIG. 10, another embodiment of a signaling device 110 is shown. In this embodiment, the signaling device also comprises a clip that extends over an edge of the absorbent article. Instead of conductive pins, however, the signaling device 110 shown in FIG. 10 includes a plurality of conductive peaks 118 that mate against corresponding stop members 119. When placed over the edge of the absorbent article, the conductive peaks form an electrical connection with the conductive zones 100 and 102.

In addition to connecting to a signaling device conductive zones formed into the outer cover of the absorbent article, in other embodiments of the present disclosure, various sensors can be placed on the outside cover of the absorbent article that can detect changes within the article and that can be in communication with a signaling device. The sensor may comprise, for instance, a temperature sensor, a conductivity sensor, a humidity sensor, a vibration sensor, a chemical sensor, or a material expansion sensor. As will be described below, each of these sensors can be placed on an exterior surface of the absorbent article and can be configured to monitor a change within the article that is indicative of the presence of a body fluid, such as urine. Each of these sensors may be used in accordance with the present disclosure without the use of the conductive zones described above. Alternatively, the conductive zones described above may be used to electrically connect one of the above sensors to a signaling device.

Figure 11:
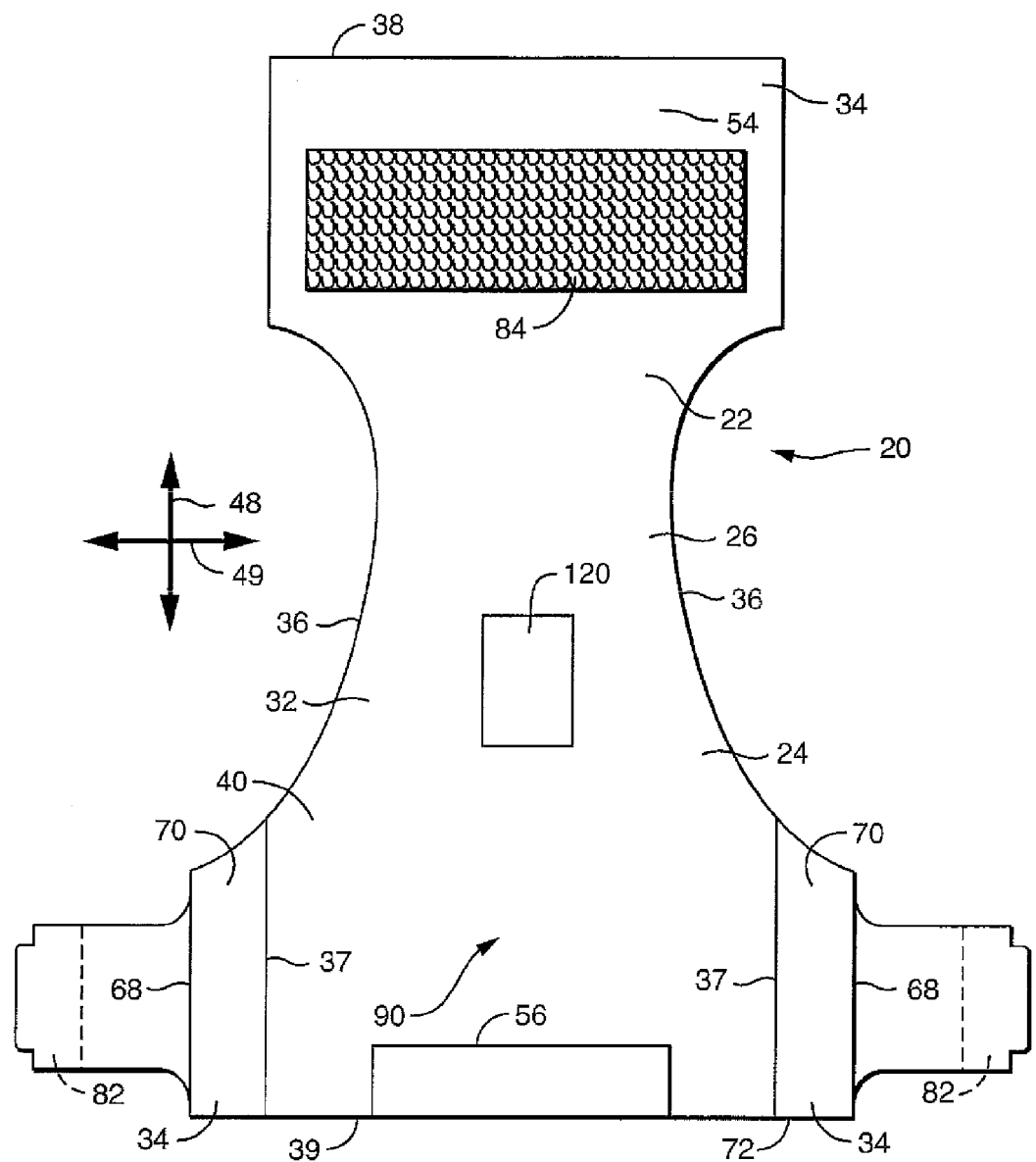
FIG. 11 is a plan view of another embodiment of an absorbent article including a signaling system in accordance with the present disclosure.

Referring to FIG. 11, one embodiment of an absorbent article that incorporates a signaling system of the present disclosure containing a sensor is shown. Like reference numerals have been used to indicate the same or similar elements. As shown, the absorbent article 20 includes a crotch region 26 separating a front region 22 and a back region 24. As described above, the absorbent article can include an absorbent structure positioned in between a liquid permeable liner and a liquid impermeable outer cover 40. The outer cover 40 includes an interior surface that faces the absorbent structure and an exterior surface as shown. In accordance with the present disclosure, mounted on the exterior surface of the outer cover 40 is a sensor 120. The sensor 120 is in communication with a signaling device. The signaling device may be located somewhere else on the absorbent article, may be remotely located, or may be integral with the sensor 120. For instance, in one embodiment, the sensor 120 and the signaling device can be contained in a single housing.

The sensor 120 is configured to sense a change in a condition within the absorbent article, such as within the absorbent structure remotely from the exterior surface of the outer cover 40. In one embodiment, for instance, the sensor 120 may comprise a temperature sensor. The temperature sensor may comprise, for instance, a thermocouple that is capable of monitoring a temperature through the outer cover 40. In an alternative embodiment, the temperature sensor may be IR driven.

When an absorbent article is insulted with a body fluid, such as urine, the fluid increases the temperature of the article where the fluid is absorbed. In particular, fluids are discharged typically at body temperature which is usually higher than the ambient temperature. The temperature sensor 120 as shown in FIG. 11 can be configured to detect the temperature increase when a body fluid has been absorbed. The signaling system can be designed such that a signaling device emits a signal when the temperature sensor 120 senses a preset temperature or senses a particular rate of temperature increase.

Figure 13:
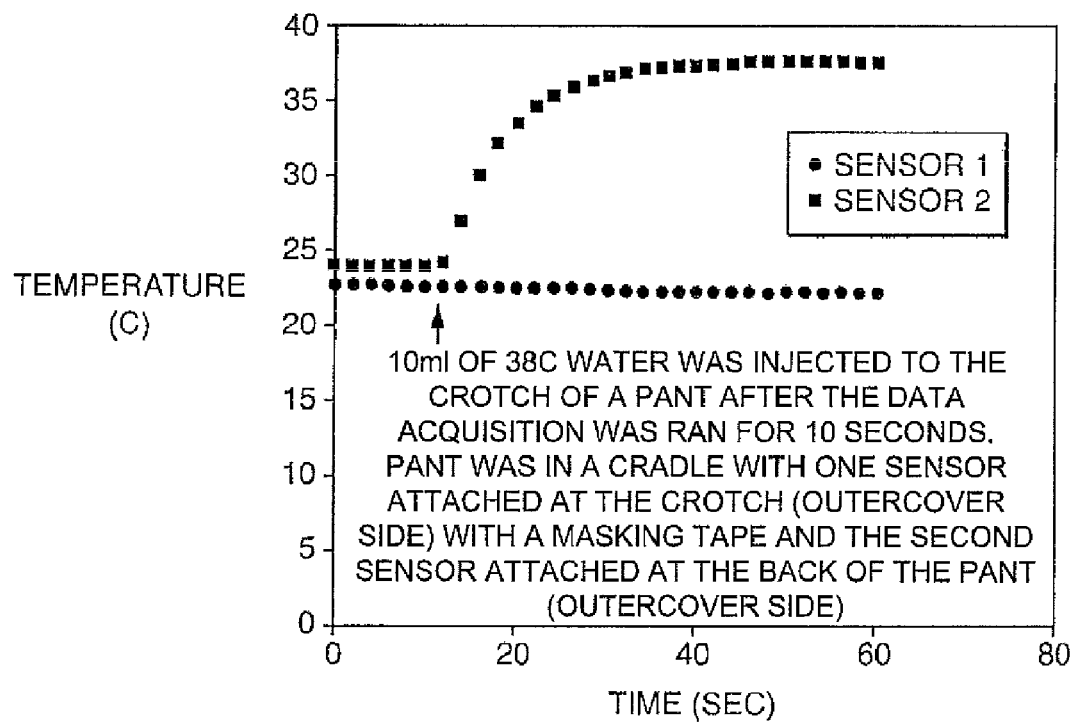
FIG. 13 are graphical representations of an experiment that was performed in accordance with the present disclosure.

In order to demonstrate the advantages of using a temperature sensor in accordance with the present disclosure, a test was conducted and the results are shown in FIG. 13. In particular, an absorbent article was placed on a mannequin. In this embodiment, the absorbent article was a pant-like article. In accordance with the present disclosure, a temperature sensor was attached to the exterior surface of the outer cover of the absorbent article at the crotch region. A second temperature sensor was attached at the back region.

Ten milliliters of water at a temperature of 38° C. was injected into the crotch region of the absorbent article. FIG. 13 is a graphical illustration of the temperatures that were sensed by the different temperature sensors. As shown, the temperature sensor attached to the exterior surface of the absorbent article on the back region consistently monitored a temperature of approximately 23° C., which was approximately the temperature of the ambient environment. The temperature sensor placed on the crotch region that monitored the temperature inside the absorbent article, however, began monitoring temperature increases after approximately 15 seconds. As shown, the temperature increased from approximately 24° C. to about 38° C. in about 15 seconds. 38° C. is approximately body temperature. As shown, the data in FIG. 13 may be used to activate a signaling device for indicating that the absorbent article has been wetted.

As described above, in one embodiment, the temperature sensor may cause the signaling device to activate or emit a signal when a preset temperature has been reached. The preset temperature, for instance, may be greater than about 32° C., such as greater than about 35° C., such as greater than about 37° C.

Alternatively, the signaling device may be configured to emit a signal when a particular temperature increase has been sensed over a particular period of time. For instance, the signaling device may be configured to emit a signal when the temperature within the article has increased by at least about 8° C. in less than about one minute, such as less than about 30 seconds.

Figure 12:
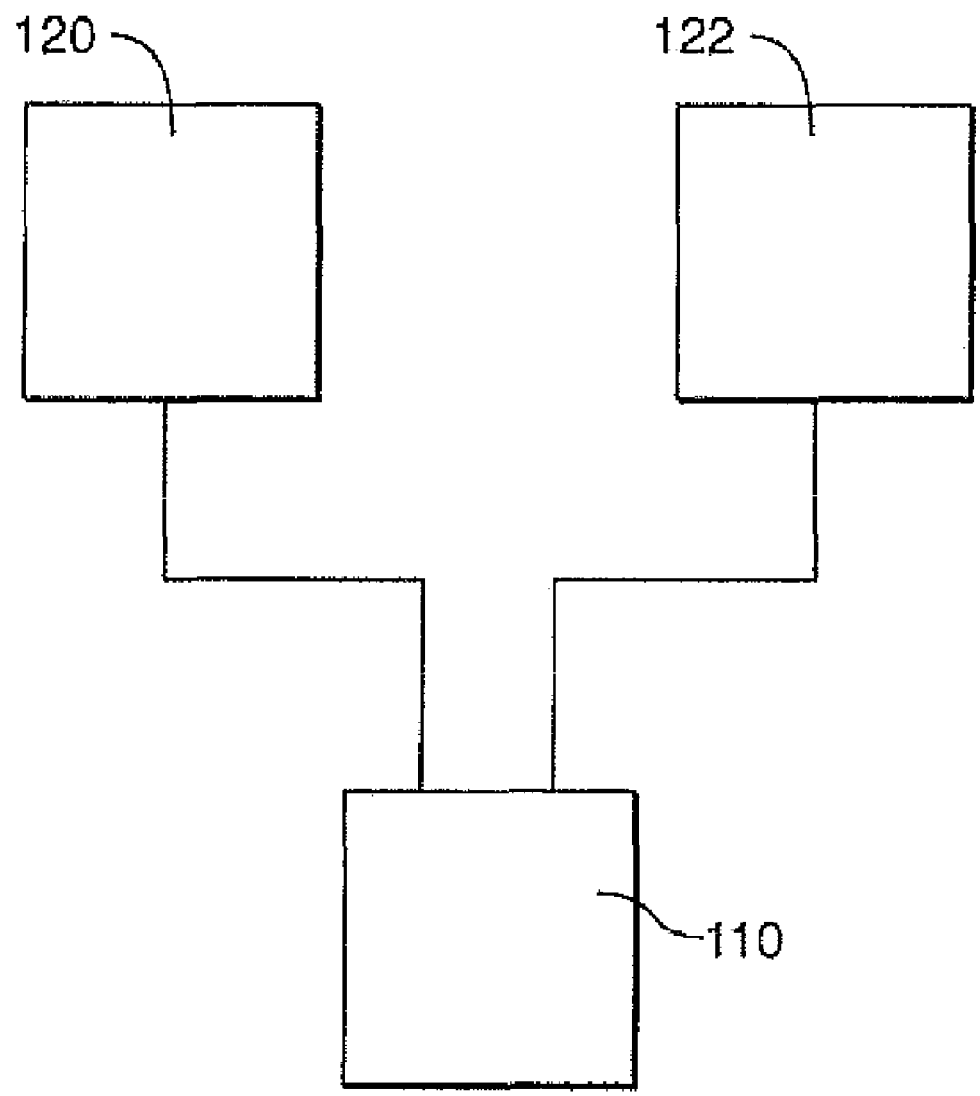
FIG. 12 is a plan view of another embodiment of a signaling system in accordance with the present disclosure.

In yet another embodiment of the present disclosure, the signaling device may be configured to emit a signal when a particular temperature differential is sensed between the temperature inside the absorbent article and the temperature outside the absorbent article. In this embodiment, for instance, the signaling system may comprise two temperature sensors as shown in FIG. 12. More particularly, the signaling system can include a first temperature sensor 120 that monitors and senses the temperature within the absorbent article and a second temperature sensor 122 that may be designed to monitor the temperature on the exterior of the absorbent article. As shown, each of the temperature sensors may be in communication with a signaling device 110. In this embodiment, the signaling device may emit a signal, for instance, when the difference in temperature between the inside of the absorbent article and the outside of the absorbent article is greater than about 8° C., such as greater than about 10° C., such as greater than about 12° C.

In the embodiment illustrated in FIG. 12, the two temperature sensors may be placed at different locations on the absorbent article. Alternatively, the temperature sensors may be incorporated into a single device. For example, the temperature sensors may be contained in a thermopile or a heat flux sensor. For example, a stack of thermocouples may be placed in series with a voltage output that is proportional to the temperature difference between the sensing directions of the sensors. Ideally, the thermopile would be configured such that one side faces the outer cover of the product and the other side faces the exterior of the product away from the wearer's body. As the temperature changes inside the product with respect to the exterior side of the product, a thermal gradient may be monitored and sensed that may be indicative of the presence of a body fluid. Alternatively, the exterior temperature of the absorbent article may not have to be measured in one linear direction with respect to the sensor that monitors the interior of the product. Various angles from the linear direct to perpendicular may apply. A change in the angle of temperature sensing may reduce the chance of the exterior temperature measurement being affected by changes in the ambient environment. The angles, for instance, may be strategically placed to take ambient measures of the near product environment to establish a baseline temperature of the outer cover for comparison to the temperature within the absorbent article.

In addition to temperature sensors, the sensor 120 as shown in FIG. 11, may comprise various other sensors that are capable of either directly or indirectly sensing the presence of a body fluid. For instance, in an alternative embodiment, the sensor 120 may comprise a humidity sensor that senses the humidity inside the absorbent article or changes in humidity. The humidity sensor 120 can be positioned on the exterior surface of the outer cover of the absorbent article as long as the outer cover is breathable. In particular, the outer cover can be constructed so as to permit humidity measurements through the material. The outer cover, however, can also be constructed to still remain liquid impermeable.

When the sensor 120 comprises a humidity sensor, the signaling system of the present disclosure can be configured to emit a signal when the humidity reaches a certain preset limit within the article. For instance, a signaling device may emit a signal when the humidity sensed within the article is greater than about 50%, such as greater than about 60%, such as greater than about 70%, such as greater than about 80%, such as greater than 90%.

Alternatively, the signaling device may be configured to emit a signal based upon a particular rate of humidity increase within the article. For instance, the signaling device may be configured to emit a signal when the humidity within the article increases by greater than 20% over a period of time of less than about two minutes, such as less than about one minute.

In still another embodiment, multiple humidity sensors may be included in the signaling system for sensing the humidity within the absorbent article and outside the absorbent article. For instance, similar to the system shown in FIG. 12, a first humidity sensor 120 may be configured to monitor the humidity inside the article, while a second humidity sensor 122 may be configured to monitor the humidity exterior to the absorbent article. In this embodiment, the signaling device 110 may be configured to emit a signal when the difference in humidity is greater than a preset limit. For exemplary purposes, for instance, the signaling device may be configured to emit a signal when the difference in humidity is greater than about 20%, such as greater than about 30%, such as greater than about 40%, such as greater than about 50%.

When the signaling system includes more than one humidity sensor, in one embodiment, the sensors can both be disposed in a single enclosure or housing. One humidity sensor, for instance, may monitor the inside of the product while another would collect data from the ambient environment. In one embodiment, the ambient sensor may be used to indicate any changes in the ambient environment that would affect measurement variability due to the location of the wearer. In this manner, a baseline humidity in the ambient environment can be calculated by the signaling system and compared to the sensor facing the interior of the absorbent article.

In still another embodiment of the present disclosure, the sensor 120 as shown in FIG. 11, may comprise a conductivity sensor that senses changes in conductivity within the interior of the absorbent article 20. Conductivity sensors are capable of monitoring changes through a material, such as the outer cover. In one embodiment, the outer cover 40 of the absorbent article may be breathable in order to assist in monitoring conditions.

In one embodiment, for instance, the conductivity sensor may generate an electromagnetic field between two parallel plates. When the plates or conductive regions are placed in proximity to a moisture containing material, the water changes the dielectric and alters the field. In this manner, the presence of moisture can almost be immediately detected.

In an alternative embodiment, the conductivity sensor may comprise one or more induction coils, such as RF (radio frequency) induction coils. For instance, each induction coil included with the sensor may be driven by an RF field. The induction coil may cause eddy currents to develop. The eddy currents can then reradiate RF energy back to the source coil, changing the impedance of the coil in the process. The change in impedance can then be measured in order to measure the change in conductivity within the article.

The impedance change in the induction coil can be measured using any suitable device, such as an oscillator. In one embodiment, for instance, a marginal oscillator may be used to measure impedance changes. A marginal oscillator, for instance, is an oscillator that operates at the threshold of oscillation. In other words, the oscillator operates with just enough feedback to sustain oscillation. In this manner, any dissipative interaction with the coil removes a fraction of the oscillator's energy, causing its output to change. Thus, the amplitude of the oscillator is very sensitive to the amount of energy dissipation or energy increase in the circuit. In one embodiment, the marginal oscillator can be combined with a detector and amplifier configured so that an increased output results when there is an increase in the conductivity of the absorbent article.

A conductivity sensor as described above is described, for instance, in U.S. patent application Ser. No. 11/511,583 and in United States Patent Application Publication No. 2008/0048786, which are both incorporated herein by reference in their entireties.

In this embodiment, the conductivity sensor 120 would be configured to sense increases in conductivity. Once a certain threshold is reached, the signaling device may then be configured to emit a signal.

In one embodiment, a conductivity enhancing agent may be incorporated into the absorbent article in order to increase the ability of the conductivity sensor to measure changes. For instance, in one embodiment, a chemical additive may be added to the absorbent structure of the article that increases changes in conductivity when wetted for better detection of body fluids.

When using a conductivity sensor that is based on the generation of an electromagnetic field, the conductivity enhancing agent may increase the absorption of the field and help distinguish absorption due to moisture, or due to the conductivity enhancing agent. The frequency of the field could be tuned to a specific conductivity enhancing agent to enhance the absorption of the radiation.

When using a temperature sensor, a humidity sensor, or a conductivity sensor as described above, in one embodiment, the system can be designed to take into account changes in the above measurements when the absorbent article is first placed on the wearer. For example, when the article is first donned, increases in temperature, humidity and conductivity can be expected. In order to account for these changes, the system of the present disclosure can be configured to only cause signals to be emitted by the signaling device when steady state conditions within the article have been reached.

For example, in one embodiment, the system can be configured such that the signaling device will not emit signals within a certain period of time once the system is first activated. The period of time can vary depending upon the particular circumstances and the particular application. For example, in one embodiment, the system may be configured not to emit signals for at least the first 15 minutes, such as at least the first 30 minutes, such as at least the first 45 minutes, such as at least the first hour the absorbent article is worn.

In an alternative embodiment, steady state is determined by the sensor used in the system. Steady state can be determined when substantial or significant changes in temperature, humidity or conductivity fail to occur for a certain period of time indicating that steady state conditions have been reached. For instance, the system may be configured to only become activated once the sensor determines no substantial changes within the interior of the article for a period of about five minutes, such as about 10 minutes, such as about 20 minutes, such as about 30 minutes, such as about 45 minutes, such as about one hour. For example, if the sensor is a humidity sensor, steady state may be determined when the humidity sensor senses no more than about 5% change in humidity on the interior of the article for a period of at least 10 minutes. A temperature sensor or a conductivity sensor may be configured in the same way.

When using a temperature sensor, a conductivity sensor, or a humidity sensor, the sensor can be placed in any suitable location on the absorbent article. For instance, the sensor may be placed in the crotch region, on the back region, or on the front region of the article depending upon various factors. As described above, in certain applications, the sensor may be placed on an exterior surface of the outer cover of the absorbent article. The outer cover can be breathable where the sensor is placed so as to facilitate monitoring of changes within the article. In fact, in certain circumstances, it may be disadvantageous for the sensor to come into direct contact with a body fluid, such as urine. For instance, if urine were to directly contact certain humidity sensors, the sensor may not operate properly. In this regard, the sensor can be placed in a location that does not come in direct contact with a body fluid or a highly breathable liquid impermeable cover may be placed around the sensor.

In still another embodiment, the sensor 120 as shown in FIG. 11, comprises a vibration sensor that senses vibrations, such as sounds, that may originate from the interior of the absorbent article. In this embodiment, for instance, a noise producing composition may be incorporated into the absorbent article. The noise producing composition, for instance, may be located on the interior surface of the outer cover or may be incorporated into the absorbent structure. The noise producing composition may comprise a composition that, when wetted, makes noise. In one embodiment, any suitable composition that creates a "fizzing" sound may be used. For instance, in one embodiment, the noise producing composition may comprise a bicarbonate alone or combined with an acid, such as tartaric acid. The sound is generated from gas formation, such as disclosed in U.S. Pat. No. 6,929,819 of Underhill, et al., which is incorporated herein. Generally, the absorbent can include an effervescent agent or combination of agents that by releasing gas and causing a mild concussive (i.e., "popping," "crackling," "bubbling" or "fizzing") sound that is distinct from ambient noise. One example of a suitable acid/base combination is shown in equation (1)

  (1)

In equation (1), sodium bicarbonate and potassium bitartrate react in the presence of a liquid (urine) to form carbon dioxide gas and by-products. The production of the carbon dioxide gas alerts the wearer of the pad containing the acid and base that urination has occurred.

Another suitable acid/base combination is shown in equation (2):

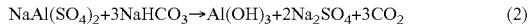  (2)

In equation (2), sodium aluminum sulfate and sodium bicarbonate react in the presence of liquid (urine) to form carbon dioxide gas and by-products. Other acids that can be used in combination with sodium bicarbonate to produce an effervescent agent in accordance with the present invention include ascorbic, lactic, glycolic, malic, tartaric, and fumaric. When mixed with sodium bicarbonate and contacted with urine, these acids produce carbon dioxide.

The signaling system in conjunction with the vibration sensor may be tuned to sense the particular sound made by the noise producing composition. Thus, when the particular sound is detected, a signaling device is configured to emit a signal.

It should be understood that the sounds produced within the absorbent article may be largely inaudible but may be detected by the sensor. The sensor may comprise, for instance, one or more microphones and signal processing hardware and software. The system may be configured to detect a particular algorithm that is indicative of vibrations being produced by the noise producing composition when wetted. Once the algorithm is detected, a signaling device may be triggered or activated so as to emit a signal indicating the presence of a body fluid.

In one embodiment, the software associated with the vibration sensor may be configured to sense noise made during urination. Thus, in this embodiment, a noise producing composition may not be needed in the interior of the article.

In yet another embodiment of the present disclosure, the sensor 120 as shown in FIG. 11 comprises an optical sensor that is configured to sense a particular color change. In this embodiment, for instance, a color changing composition may be incorporated into the absorbent article. The color changing composition may be designed to change color when wetted. The color changing composition may be contained within the absorbent structure. Alternatively, the color changing composition may be incorporated into the sensor itself or positioned opposite the sensor on the interior surface of the outer cover. In this embodiment, the outer cover can be constructed so that the optical sensor can sense color changes through the outer cover of the absorbent article.

The color changing composition, as described above, may change color when wetted. Alternatively, the color changing composition may change color based upon a pH change or when contacted with a chemical compound typically contained in urine or a vapor contained in urine.

In one particular embodiment, the color changing composition may comprise bromocresol green dye. Bromocresol green dye is sensitive to pH. When the pH changes, the bromocresol green dye changes to blue. The optical sensor may be configured to read the color change and cause a signaling device to emit a signal.

In other embodiments, the color changing composition may comprise a washable ink especially if the sensor is positioned on a colored portion of the absorbent article. In this embodiment, when the absorbent article is wetted, the ink is washed from the spot on the product and the sensor would sense the change in color intensity or absence of color.

In another embodiment of the present disclosure, the sensor 120 may comprise a chemical sensor that is configured to sense the presence of a particular chemical species. In this embodiment, a chemical indicating composition may be present in the absorbent article that, when wetted, produces the chemical species. Alternatively, the chemical sensor may be configured to sense a particular chemical compound found in urine.

The sensor 120 or the outer cover 40 of the absorbent article can be constructed so as to be able to sense the chemical species through the outer cover. The chemical species may comprise either a gas or a liquid.

In one embodiment, for instance, the outer cover of the absorbent article may be breathable.

In one embodiment, for instance, the chemical sensor may be configured to sense the presence of carbon dioxide. Various different chemical indicating compositions are available that, when contacted with urine, would produce copious amounts of carbon dioxide for detection. For instance, in one embodiment, the chemical indicating composition may comprise an organic acid in combination with a carbonate. Such carbonates can include, for instance, sodium carbonate or sodium bicarbonate. The organic acid may comprise, for instance, ascorbic acid, lactic acid, tartaric acid, citric acid, oxalic acid, or polymeric carboxylic acids, such as polyacrylic acids. Such acids react with sodium carbonate or sodium bicarbonate to generate carbon dioxide in the presence of water or urine. The organic acids and the carbonate can be in the form of a grain, powder or can be encapsulated in water soluble matrices such as carbohydrates (e.g. sugars), salts (e.g. sodium chloride), etc. In this way, the composition does not produce carbon dioxide unless water or urine is present.

In an alternative embodiment, a chemical sensor may be configured to sense the presence of nitrogen. Similar to carbon dioxide, nitrogen is odorless and safe. In this embodiment, the chemical indicating composition may comprise sulfamic acid and sodium nitrite which rapidly produces nitrogen in the presence of water. Both chemicals are not reactive in a dry state. Thus, the composition can be added in the form of a tablet, a powder or encapsulated in a water soluble matrix. Once contacted with urine, however, the composition will produce copious amounts of nitrogen that can be sensed by the chemical sensor.

When using a chemical sensor as described above, the sensor may not need to be placed in the crotch region as shown in FIG. 11. Instead, the sensor may be placed anywhere on the article, such as on the waistband, where the release of gases may occur. Alternatively, the sensor may be placed anywhere on the outer cover as long as gases can be detected through the outer cover.

In still another embodiment, the chemical sensor may comprise a volatile organic compound sensor. In this embodiment, a volatile organic compound may be placed in association with the absorbent article, such as on the inside of the article or directly in association with the sensor. Once contacted with water, a volatile organic compound may be produced that can then be sensed. Sensing the volatile organic compound will cause the signal device to emit a signal.

In yet another embodiment of the present disclosure, the sensor 120 may comprise a material expansion sensor that is configured to detect when a certain portion of the absorbent article increases in size due to the article absorbing substantial amounts of a liquid, such as urine. Once a material expansion is detected, a signaling device is configured to emit a signal indicating the presence of a body fluid.

In one embodiment, for instance, the material expansion sensor may comprise a strain gauge. The strain gauge may be adapted to measure the expansion of the outer cover, or any other component on the absorbent article. Strain gauge devices are described, for instance, in U.S. Pat. No. 5,454,376.

All of the sensors described above can be configured to be disposed of with the absorbent article. When disposable, the sensor can be integrated into the outer cover of the article. For instance, in one embodiment, the outer cover may comprise more than one layer and the sensor may be positioned in between the two layers.

In an alternative embodiment, the sensor can be configured to be removed from the absorbent article when the article is disposed and placed on a new article. In fact, in one embodiment, the sensor and/or signal device can include multiple settings depending upon the absorbent article to which it is attached. In this manner, the signaling system can be modified based upon the particular product specifications.

For instance, in certain embodiments the breathability of the outer cover may impact the effectiveness of the sensor. In one embodiment, the signaling system may include different settings depending upon the breathability of the outer cover of the particular product used in conjunction with the signaling system. For example, the signaling system may include an algorithm which is a function of the product specifications (e.g. breathability and/or absorbence) and the signaling criteria may be based in part on the algorithm.

In one particular example, for instance, the humidity sensor may function differently depending upon the breathability of the outer cover of the absorbent article. According to the present disclosure, the humidity sensor may include different settings that are dependent upon the particular breathability of the outer cover of the product used in association with the sensor. The product purchased, for instance, may provide information to the consumer as to which setting to use.

As absorbent articles increase in effectiveness, in one embodiment, the signaling system of the present disclosure may be configured to emit a signal or not emit a signal during a first insult of urine and/or to emit a signal when a second insult occurs. In one embodiment, for instance, the absorbent article may be constructed so as to be capable of holding two insults of urine from the wearer. A wetness sensing system may be particularly needed for these types of articles so that a caregiver can differentiate between the first insult and the second insult. In accordance with the present disclosure, the signaling system can be constructed so as to recognize a change within the absorbent article due to the first insult and then readjust the criteria based upon the second insult. Once the second insult is recognized, the signaling system can be designed to emit a signal.

For instance, in one embodiment, the sensor may comprise a humidity sensor. After a first insult with urine, the humidity sensor may sense a humidity within the article within a first range, such as from about 60% to about 80%. After the second insult, however, the sensor may be configured to sense humidity within a second range. The second range, for instance, may overlap with the first range or be separate. In one embodiment, for instance, the second range may be greater than 80%, which can then be used to differentiate between first insults and second insults of the article.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
    an outer cover having an interior surface and an exterior surface;
    an absorbent structure positioned adjacent the interior surface; and
    a first conductive zone spaced from and discrete from a second conductive zone, the conductive zones being located on the outer cover, each conductive zone comprising an area on the outer cover that defines a plurality of apertures that extend through the outer cover, the apertures being covered by a conductive composition.

2. An absorbent article as defined in claim 1, wherein the absorbent article includes a crotch region positioned in between a front region and a back region, and wherein the first conductive zone and the second conductive zone extend into the crotch region.

3. An absorbent article as defined in claim 1, wherein the conductive composition comprises a conductive ink that has been applied over the apertures.

4. An absorbent article as defined in claim 1, wherein the conductive composition comprises a conductive adhesive that has been applied over the apertures.

5. An absorbent article as defined in claim 1, further comprising a signaling device that is configured to make an electrical connection with the first conductive zone and the second conductive zone, the signaling device producing a signal when a conductive substance present in the absorbent article makes an electrical connection between the first conductive zone and the second conductive zone.

6. An absorbent article as defined in claim 1, wherein the apertures in the first conductive zone and in the second conductive zone have a diameter of from about 0.1 mm to about 1.5 mm.

7. An absorbent article as defined in claim 6, wherein the apertures are present in the first conductive zone and in the second conductive zone at a density of from about 10 apertures per $cm^2$ to about 50 apertures per $cm^2$.

8. An absorbent article as defined in claim 5, wherein the signaling device comprises a clip that extends over an edge of the article for making the electrical connection to the first conductive zone and the second conductive zone, includes a hook-type material capable of forming an attachment with the outer cover of the absorbent article for making an electrical connection with the first conductive zone and the second conductive zone or, includes a conductive adhesive that attaches the signaling device to the first conductive zone and to the second conductive zone on the absorbent article.

9. An absorbent article comprising:
    an outer cover having an interior surface and an exterior surface;
    an absorbent structure positioned adjacent the interior surface of the outer cover; and
    a signaling system comprising a sensor that is attached to the outer cover and is configured to sense a change in a condition within the absorbent structure, the sensor comprising a temperature sensor, a conductivity sensor, a humidity sensor, a vibration sensor, a chemical sensor, or a material expansion sensor, the signaling system further including a signaling device that emits a signal when a change in a condition within the absorbent structure is sensed by the sensor.

10. An absorbent article as defined in claim 9, wherein the sensor comprises a temperature sensor.

11. An absorbent article as defined in claim 10, wherein the signaling device is configured to emit a signal when the temperature sensor senses a temperature within the absorbent article of greater than about 32° C.

12. An absorbent article as defined in claim 10, wherein the signaling device is configured to emit a signal when the temperature sensor senses an increase in temperature in the absorbent article of greater than about 8° C. in less than about one minute.

13. An absorbent article as defined in claim 9, wherein the sensor comprises a first temperature sensor and a second temperature sensor, the first temperature sensor sensing a temperature within the absorbent structure, the second temperature sensor sensing a temperature exterior to the absorbent article, the signaling device emitting a signal when the temperature difference between the first temperature sensor and the second temperature sensor exceeds a preset limit.

14. An absorbent article as defined in claim 9, wherein the sensor comprises a conductivity sensor.

15. An absorbent article as defined in claim 14, wherein the conductivity sensor comprises an RF induction coil that senses changes in impedance.

16. An absorbent article as defined in claim 15, wherein the changes in impedance are measured by an oscillator.

17. An absorbent article as defined in claim 9, wherein the sensor comprise a humidity sensor.

18. An absorbent article as defined in claim 17, wherein the signaling device is configured to emit a signal when the humidity sensor senses an increase in humidity in the absorbent article of more than 20% in 60 seconds.

19. An absorbent article as defined in claim 9, wherein the sensor comprises a first humidity sensor and a second humidity sensor, the first humidity sensor sensing humidity within the absorbent structure, the second humidity sensor sensing humidity exterior to the absorbent article, the signaling device emitting a signal when the humidity difference between the first humidity sensor and the second humidity sensor exceeds a preset limit.

20. An absorbent article as defined in claim 9, wherein the sensor includes different settings that are selected by the user depending upon at least one specification of the absorbent article.

21. An absorbent article as defined in claim 20, wherein the outer cover of the absorbent article is breathable and wherein the sensor is configured to sense a change in a condition within the absorbent structure through the breathable outer cover and wherein the sensor includes a plurality of settings depending upon the breathability of the outer cover.

22. An absorbent article as defined in claim 9, wherein the signaling system is configured to differentiate between a first insult of the absorbent article with a body fluid from a second insult of the absorbent article with a body fluid.

23. An absorbent article as defined in claim 9, wherein the outer cover is breathable and wherein the sensor is configured to sense changes in a condition within the absorbent structure through the breathable outer cover.

24. An absorbent article as defined in claim 9, wherein the sensor comprises a temperature sensor, a conductivity sensor, or a humidity sensor and wherein the signaling system is configured to discern a steady state environment within the absorbent article after the article is donned before being configured to emit a signal by the signaling device.

25. An absorbent article as defined in claim 24, wherein the sensor comprises a humidity sensor.

26. An absorbent article as defined in claim 9, wherein the sensor comprises a vibration sensor, and wherein the absorbent article contains a noise-producing composition that produces vibrations when wetted, the vibration sensor being configured to sense vibrations produced by the noise-producing composition causing the signaling device to emit a signal.

27. An absorbent article as defined in claim 26, wherein the vibration sensor comprises a microphone.

28. An absorbent article as defined in claim 9, wherein the sensor comprises a chemical sensor, and wherein the absorbent article contains a chemical indicating composition that releases a chemical species when wetted, the chemical sensor being configured to detect the presence of the chemical species within the absorbent article causing the signaling device to emit a signal.

29. An absorbent article as defined in claim 28, wherein the chemical species comprises a gas.

30. An absorbent article as defined in claim 28, wherein the chemical species comprises a liquid.

31. An absorbent article as defined in claim 28, wherein the chemical sensor comprises a volatile organic compound sensor and wherein the chemical species comprises a volatile organic compound.

32. An absorbent article as defined in claim 28, wherein the chemical species comprises carbon dioxide or nitrogen.

33. An absorbent article as defined in claim 9, wherein the sensor comprises an optical sensor, and wherein the absorbent article contains a color-changing composition that changes color when wetted, the optical sensor being configured to sense the color change causing the signaling device to emit a signal.

34. An absorbent article as defined in claim 9, wherein the sensor comprises a material expansion sensor that is configured to sense an expansion in the absorbent article at a particular location, and wherein the signaling device is configured to emit a signal when the absorbent article expands a preset distance.

35. An absorbent article as defined in claim 34, wherein the material expansion sensor comprises a strain gauge.

36. An absorbent article as defined in claim 9, wherein the sensor comprises a chemical sensor that is configured to detect the presence of a chemical species that is found in urine.

37. An absorbent article as defined in claim 36, wherein the chemical species comprises ammonia.

* * * * *